US012496463B2

(12) United States Patent
De Vries et al.

(10) Patent No.: US 12,496,463 B2
(45) Date of Patent: Dec. 16, 2025

(54) SELECTOR FOR REMOTE MEDICAL ELEMENT POSTIONING

(71) Applicant: NUCLETRON OPERATIONS B.V., Veenendaal (NL)

(72) Inventors: Frits Pieter De Vries, Renkum (NL); Luuk Schouten, Veenendaal (NL); Aalt Jacob Welgraven, Veenendaal (NL)

(73) Assignee: Nucletron Operations B.V., Veenendaal (NL)

( * ) Notice: Subject to any disclaimer, the term of this patent is extended or adjusted under 35 U.S.C. 154(b) by 932 days.

(21) Appl. No.: 17/754,089

(22) PCT Filed: Sep. 30, 2020

(86) PCT No.: PCT/NL2020/050604
§ 371 (c)(1),
(2) Date: Mar. 23, 2022

(87) PCT Pub. No.: WO2021/066648
PCT Pub. Date: Apr. 8, 2021

(65) Prior Publication Data

US 2022/0370828 A1 Nov. 24, 2022

(30) Foreign Application Priority Data

Sep. 30, 2019 (NL) ..................................... 2023918

(51) Int. Cl.
*A61N 5/10* (2006.01)

(52) U.S. Cl.
CPC .... *A61N 5/1007* (2013.01); *A61N 2005/1012* (2013.01)

(58) Field of Classification Search
CPC .......... A61N 5/1007; A61N 2005/1008; A61N 2005/1018; A61N 5/1014–1017; A61N 2005/1024; A61N 2005/1025
See application file for complete search history.

(56) References Cited

U.S. PATENT DOCUMENTS 5,120,973 A 6/1992 Rohe et al.
6,752,753 B1 6/2004 Hoskins et al.
(Continued)

FOREIGN PATENT DOCUMENTS

CN 1233430 C 12/2005

OTHER PUBLICATIONS

"European Application No. 20 785 860.6, Communication pursuant to Article 94(3) EPC dated Feb. 14, 2025", (Feb. 14, 2025), 3 pgs.
(Continued)

*Primary Examiner* — Carrie R Dorna
(74) *Attorney, Agent, or Firm* — Schwegman Lundberg & Woessner, P.A.

(57) ABSTRACT

The invention relates to a medical device for transporting and positioning a therapeutic emitting element into a treatment channel to be temporarily placed in or at the body of the patient to treat tumours. The therapeutic emitting element is connected to a transport element and which is driven by at least one drive motor. The device has a connecting element comprising multiple connector openings. The connecting element is used for connecting a transport tube to a respective connector opening. The transport tube is connected to an applicator, needle, tube or catheter for driving the transport element into the treatment channel. The device has a selector mechanism through which the plurality of transport elements are driven. An annular guiding arrangement guides the transport elements into connector openings in the connecting element. The annular guiding arrangement also comprises a plurality of spaced outlets. The inlets of the multiple patterns are each connected to an outlet by guiding channels. Each outlet aligns to a connector opening in the connecting element to allow the transport element from each outlet to be driven into the connector openings.

12 Claims, 13 Drawing Sheets

(56) References Cited

U.S. PATENT DOCUMENTS

| | | | | |
|---|---|---|---|---|
| 2005/0261539 | A1* | 11/2005 | van't Hooft | A61N 5/1007 600/2 |
| 2013/0204072 | A1 | 8/2013 | Verard et al. | |
| 2016/0000519 | A1 | 1/2016 | Dehghan Marvast | |

OTHER PUBLICATIONS

"International Application No. PCT/NL2020/050604, International Search Report dated Mar. 17, 2021", (Mar. 17, 2021), 6 pgs.

"International Application No. PCT/NL2020/050604, Written Opinion dated Mar. 17, 2021", (Mar. 17, 2021), 7 pgs.

"Chinese Application No. 202080068325.7, Office Action dated Apr. 28, 2025", w English Translation, (Apr. 28, 2025), 16 pgs.

* cited by examiner

SELECTOR FOR REMOTE MEDICAL ELEMENT POSTIONING

PRIORITY APPLICATIONS

This application is a U.S. National Stage Filing under 35 U.S.C. § 371 from International Application No. PCT/NL2020/050604, filed on Sep. 30, 2020, and published as WO2021/066648 on Apr. 8, 2021, which claims the benefit of priority to Netherlands Application No. 2023918, filed on Sep. 30, 2019; the benefit of priority of each of which is hereby claimed herein, and which applications and publication are hereby incorporated herein by reference in their entireties.

FIELD OF THE INVENTION

The present invention is in the field of medical treatment. In particular, the invention is in the field of treating tumours.

BACKGROUND OF THE INVENTION

Brachytherapy is a form of radiotherapy that uses at least one radioactive capsule (sealed source) or X-ray source which are temporarily inserted into or onto the body of a patient in close proximity to or inside of a tumour. In this way radioactive damage to healthy tissue may be reduced compared to external radiation therapy and may lead to more efficient treatment A type of brachytherapy device generally referred to as a brachytherapy after loader is described in US20050261539 having a radioactive source, which is placed temporarily in the body of a patient. The radioactive source is transported from a shielded safe by a (at least partial) flexible transport element (e.g. wire, wire-rope, composite structure, tube). The transport element is driven by a motor via a switch (selector mechanism) along a transport tube to an applicator. The applicator may connect hollow needles with the transport tubes that receive the transport element (including the capsule) into the body of the patient. In a similar way, it is possible to treat or ablate abnormal tissue through the use of transport elements with another type of a therapeutic emitting element in the distal area, such as a laser or optical fiber for laser ablation or targeted light therapy, or other elements for focused ultrasound, HIFU, thermotherapy, etc. Besides a transport element with an emitting element for therapeutic application often also one or more other transport elements are sent out before or during the treatment to ensure that the treatment goes well (e.g. a dummy-source cable, electromagnetic tracking sensor cable, in-vivo dosimetry cable, optical sensor cable, inductance sensor cable, etc.) The switch is able to accommodate multiple transport elements with multiple motors. A rotatable part of the switch may switch transport elements between different transport tubes by carrying a coupling element that contains a transport element to a transport tube. The main function of the switch is to ensure that all applied transport elements can be sent in any desired transport tube, whereby the entire treatment can be carried out safely and as quickly as possible. But the switch appears to be limited in the availability of transport tubes that can be switched to, due to adjacent transport wires blocking the path to some transport tubes. Further a supporting arm prevents the switch from rotating a full revolution. The implication of the adjacent coupling elements and transport elements blocking the path of some transport elements to move to other transport tubes is that the adjacent coupling elements and feed elements need to be retracted and displaced prior to a particular coupling element and transport element is able to move. The displacement and relocation of adjacent coupling elements can be a time consuming operation which may delay or impact the therapy. In the case of three drive motors and three elements there is also the danger of hedging a coupling element between the supporting arm and two adjacent coupling elements which may more than double the delay. Another possible disadvantage is the obscuring nature of the switch in that it may be difficult to detect that the coupling element has successfully connected with the correct transport tube and also that the transport tube connector is mounted by the device operator in the correct switch opening and deep enough in the switch before the connector locking mechanism in the switch is activated and the transport elements are sent out. Early detection of errors in the mounting of the transport tubes or switching operation can prevent jamming or delay in the duration of the therapy, or at worst prevent delivering the therapeutic emitting element to the incorrect location or not at all.

SUMMARY OF THE INVENTION

The invention provides for solving or improving at least one of the disadvantages of the prior art by a device used for remotely transporting and positioning at least one transport element, in which a therapeutic emitting element is present, into at least one applicator, needle, tube or catheter, to be temporarily placed in or at the body of a patient. The device is provided with a plurality of transport elements with a therapeutic emitting element in or near the distal area of the plurality of transport elements; the plurality of transport elements being slidable by at least one drive motor. The device is also provided with a connecting element comprising multiple connector openings. The connecting element is used for connecting a transport tube connector to a respective connector opening. The transport tube is connected to a treatment channel, being e.g. an applicator, needle, tube or catheter, for driving the transport elements through the connector openings and transport tube to the intended treatment area. The device has a selector mechanism (switch) through which the plurality of transport elements are driven. The selector mechanism has a plurality of independently displaceable selector channels. Each selector channel corresponds to one of the transport elements so that the plurality of transport elements are able to be driven through the said selector channels. The selector channel can then direct the plurality of transport elements into the treatment channel connected to the connecting element.

Further, the device is provided with a guiding arrangement for guiding the plurality of transport elements into corresponding connector openings in the connecting element. The guiding arrangement comprises a plurality of inlets in a front surface of the annular guiding arrangement, which faces away from the connecting element. The guiding arrangement also comprises a plurality of spaced outlets in a rear surface thereof facing the connecting element. Each outlet connects to a respective connector opening in the connecting plate to allow the transport element from each outlet to be driven into the connector openings. The outlets of the guiding arrangement are each connected to more than one inlet in the guiding arrangement by guiding channels formed in the guiding arrangement.

In an another aspect a device is provided for transporting and positioning at least one emitting element for therapeutic application into at least one treatment channel to be temporarily placed in or at the body of a patient comprising at least one transport element; said emitting element in the distal area of the transport element, and said transport element being slidable by at least one drive motor; a connecting element comprises multiple connector openings, for connecting a transport tube to a respective connector opening, which transport tube is connectable to a treatment channel for driving the transport elements through the connector openings and transport tube to the treatment channel. A selector mechanism is provided through which the transport element is driven, said selector mechanism comprising a selector channel; wherein said selector channel corresponds to the transport element; wherein said transport element is driven through said selector channel for directing the said transport element into said connecting element; wherein a detector is arranged about central to the connecting element to detect a position of a transport tube and/or a position of a selector channel. By a central position of the detector conveniently an omnidirectional view can be provided to assess the connections in the connector element individually.

DETAILED DESCRIPTION

The invention provides a device for transporting and positioning at least one therapeutic emitting element (e.g. capsule 1, in which a radioactive source is present). The capsule may house a radioactive source as known in the art of brachytherapy and by attaching the capsule to a transport element, e.g. wire the radiation source may be transported by reeling the transport wire in or out.

Figure 1:
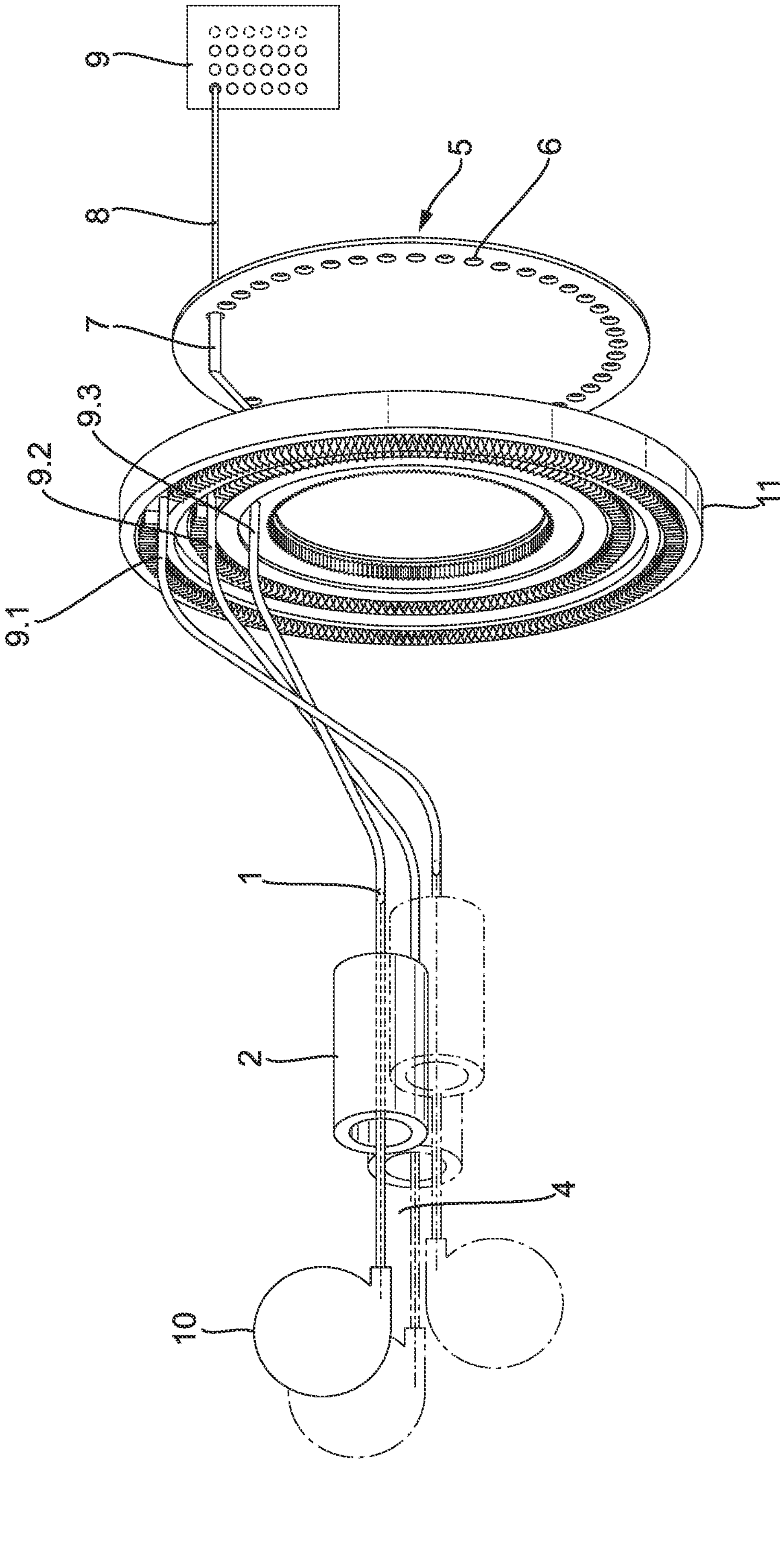
FIG. 1 shows an exploded view of an embodiment of the invention.

In FIG. 1 an embodiment of the invention is shown with a capsule 1 which may be transported from a screened safe 2 into at least one treatment channel (e.g. a needle, catheter, tube or a source guiding channel of an applicator) to be temporarily placed in or at the body of the patient. The device is provided with at least one therapeutic emitting element (e.g. radiation capsule 1) and a plurality of transport wires 4. The capsule 1 may be connected with one end of one of the transport wires 4, and the plurality of transport wires 4 may slide when one of the drive motors 10 drives the associated transport wire 4. The device may be equipped with a safe 2 for storing radiation capsule 1 and may be provided with an outlet for taking the radiation capsule 1 into and out of the safe 2 when the transport wire 4 is driven. The safe prevents the radiation from the radiation sources inside the safe from causing radioactive damage to unintended objects or persons and even the patient outside the safe while the radiation sources are stored.

Further, a connecting element (e.g. plate) 5 of the device is shown which has multiple connector openings 6. Each connector opening 6 can connect to one connector attached to a transport tube 8 and one or more transport tubes connect to an applicator 9, so that the transport wires 4 may be driven through the connector openings 6 and transport tube 8 to the intended treatment channel. Typically an applicator has multiple treatment channels to ensure a proper dose distribution to the tumour or target location inside the patients body.

The device has a selector mechanism 11 through which the plurality of transport wires 4 are driven. The selector mechanism 11 holds a plurality of selector channels 9 (e.g. 9.1, 9.2 and 9.3) that each corresponds to one of the transport wires 4. The transport wires 4 may be driven through the selector channels 9.1, 9.2, 9.3 to direct the transport wires 4 into the connecting plate 5. Through entering the connector plate 5 the driven transport wire 4 may enter a transport tube 8 which leads to a treatment channel In FIG. 2 an embodiment of the invention is shown with an guiding arrangement 20 which guides the plurality of transport wires 4 into corresponding connector openings 6 into the connecting element, e.g. plate 5. While the guiding arrangement 20 is annular in shape, other, e.g. rectangular shapes of a guiding arrangement, in combination with a connecting element may also be used. Furthermore, the guiding arrangement may be preferably static relative to the connector plate but may also be designed movable; e.g. with the selector channels. In that case the guiding arrangement comprises a plurality of guiding elements or blocks that move along with the selector channels.

The guiding arrangement 20 comprises a plurality of inlets 21 spaced in multiple patterns 21.1, 21.2, 21.3 along a circumference in a front surface of the guiding arrangement 20 which faces away from the connecting plate 5. By forming concentric patterns of inlets 21 a particular pattern of inlets may be dedicated to accepting a transport wire from one selector channel, although this is not necessary for the invention, e.g. also a linear arrangement of inlets is possible. Each pattern 21 having a different radius from the centre axis of the guiding arrangement 20 along the front surface to match the corresponding selector channel. In this way a selector channel may be moved to any location without being blocked by another selector channel which reduces the after loading time required to perform the therapy. The front surface of the guiding arrangement 20 may also be shaped so that the front surface is perpendicular to each guiding channel at the location of each inlet. The inlets 21 of the guiding channels (see FIG. 3) may also be flared to form a larger opening for the transport wire 4 to enter and so reduce the likely hood of the transport wires 4 jamming during transitioning from one part of the invention to another.

Figure 2:
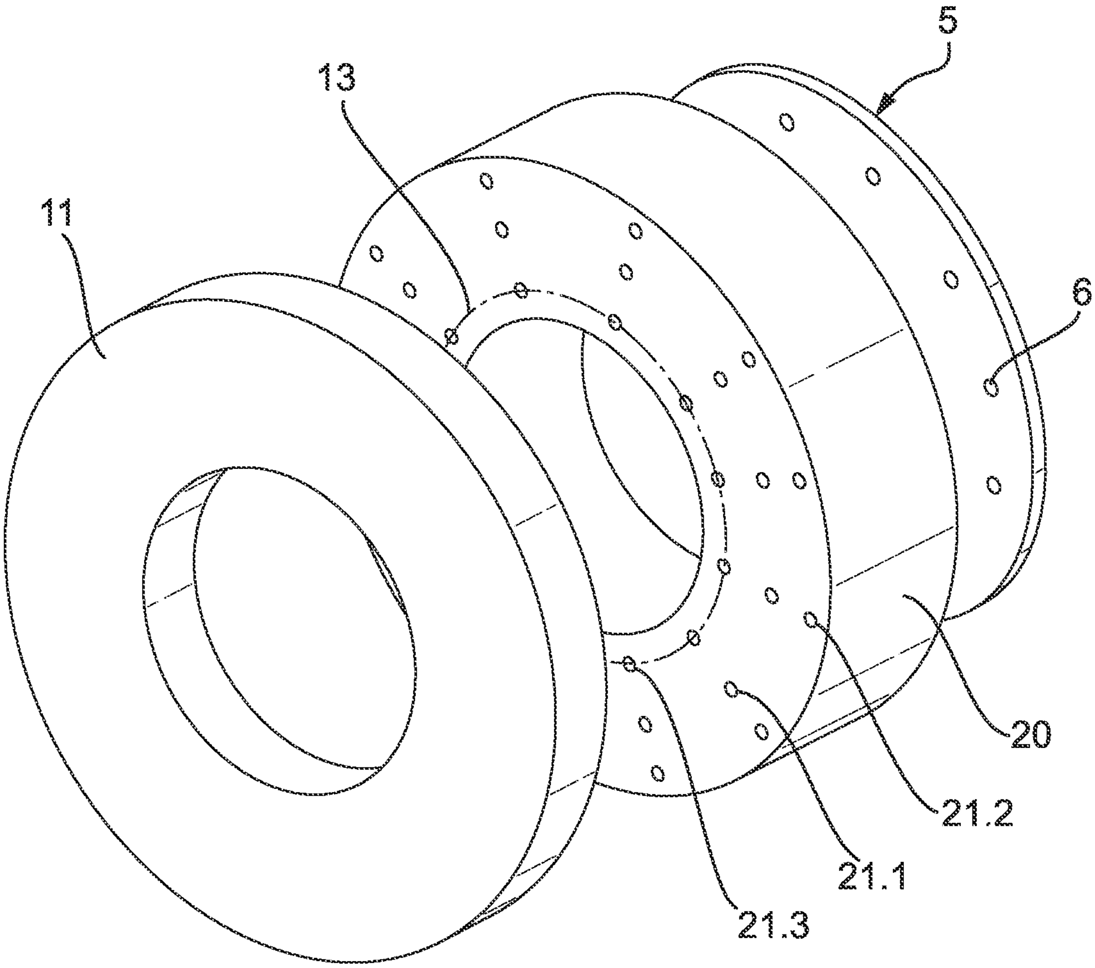
FIG. 2 shows an embodiment of the invention with an annular guiding arrangement.
Figure 3:
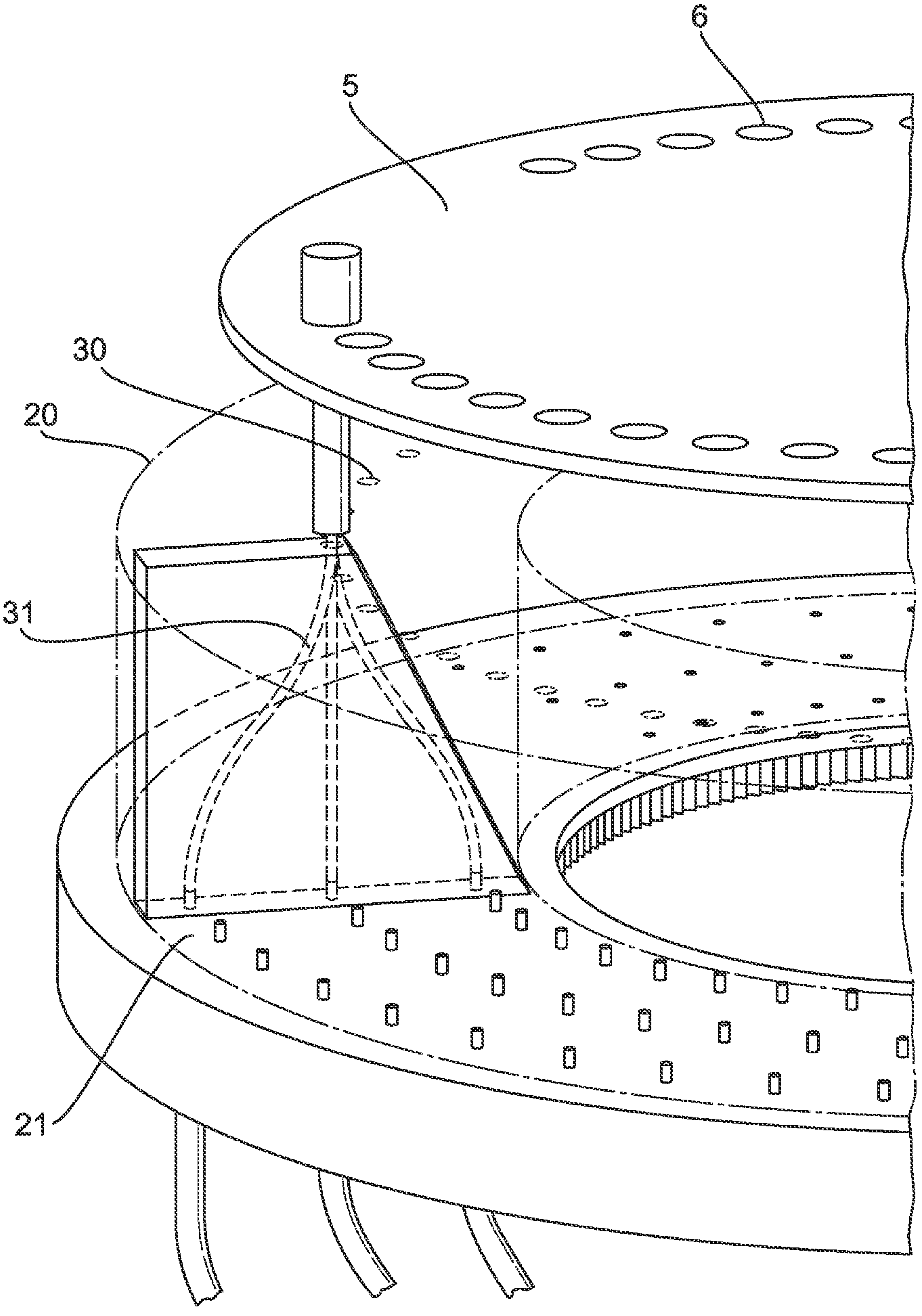
FIG. 3 shows a partial view of an embodiment of the invention with an annular guiding arrangement.

In FIG. 3 part of an embodiment of the invention is further shown with the guiding arrangement 20 which has multiple spaced outlets 30 in a rear surface facing the connecting plate 5. The outlets 30 (shown in FIG. 2) are each connected to more than one respective inlet 21 by guiding channels 31 branching an outlets to multiple inlets formed in the guiding arrangement 20. Each outlet 30 aligns to a respective connector opening 6 in the connecting plate 5 to allow the transport wire 4 fed through each outlet 30 to be driven into the connector openings 6. The guiding arrangement 20, outlets 30 and selector mechanism may preferably be radial spaced, (partly) have openings or made of transparent material, and/or concentrically chamfered so as to facilitate tracking of the and content of the guiding channels 31 or to reduce manufacturing costs.

The selector channels 9 (shown in FIG. 1) of the selector mechanism 11 are arranged to revolve independently from each other around a central axis to follow the plurality of spaced selector ring or inlets 21 (shown in FIG. 2). The purpose of the guiding arrangement is to allow the option of all transport wires gaining access to a particular transport tube so that an outlet of the guiding arrangement is effectively shared between the different transport wires once any wire 4 in the transport tube 8 has been retracted out of the guiding arrangement 20.

Figure 4:
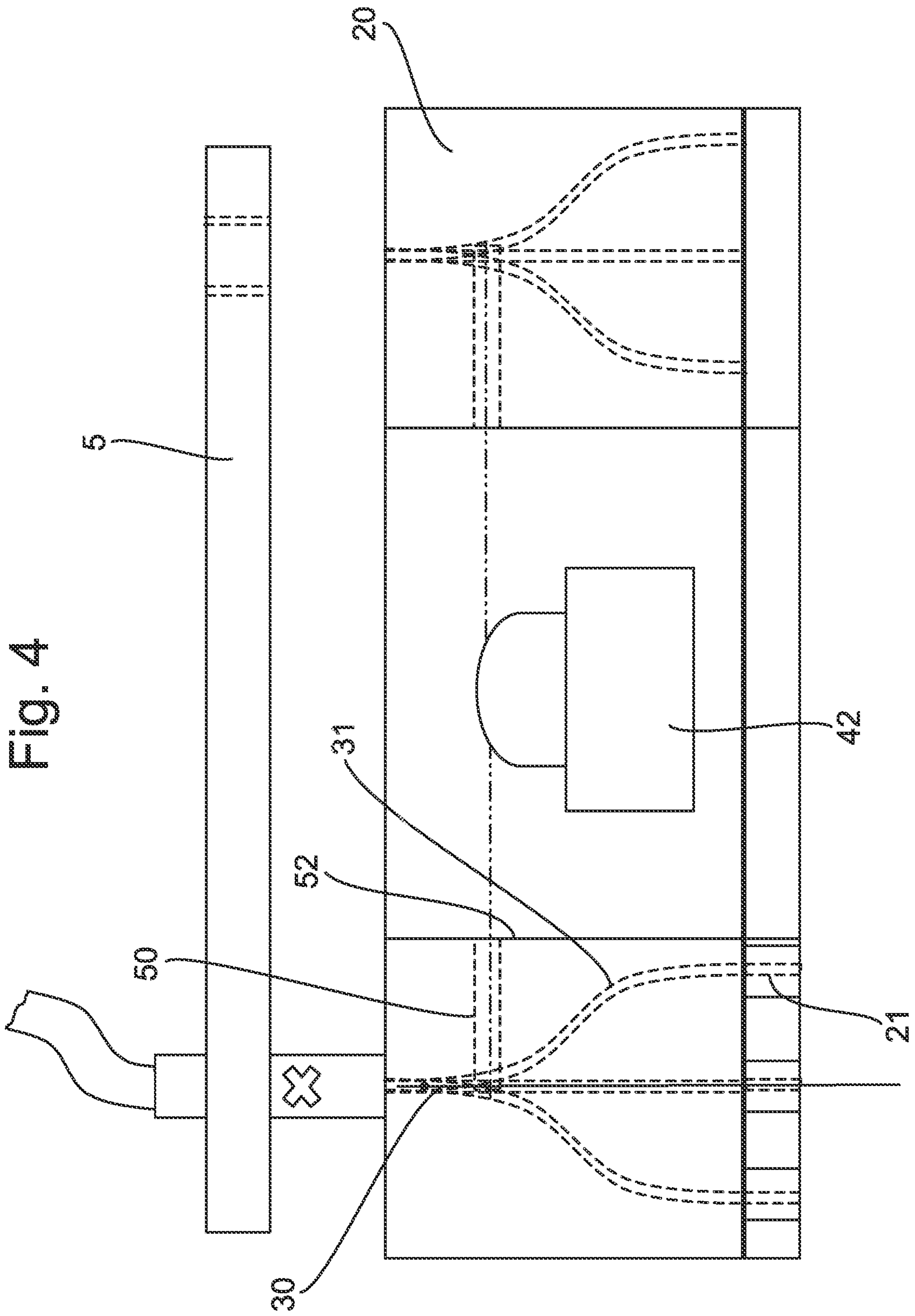
FIG. 4 shows a cross sectional view of an embodiment of the invention.

In FIG. 4 a cut away of an embodiment of the invention is shown with the guiding arrangement 20 having at least one view port 50 situated in an inner surface 52 central to the guiding arrangement 20. The content of at least one guiding channel 31 is visible through the respective view port 50 by optical detector 42. The view port 50 serves as a means for detecting the presence of a transport wire 4 or detecting of the most distal position of the transport wire, therapeutic emitting element, or capsule and may also serve as a means for identification or checking the correct transport wire or radiation source has been loaded. The view port 50 may further help to detect the location of jammed or other errors in the transporting, functioning or quality of the transport wire, therapeutic emitting element, or capsule 1 (shown in FIG. 1). In an embodiment, this optical detector arrangement can be provided without the guiding arrangement; e.g. to monitor the connector openings by an omnidirectional view camera.

Figure 5:
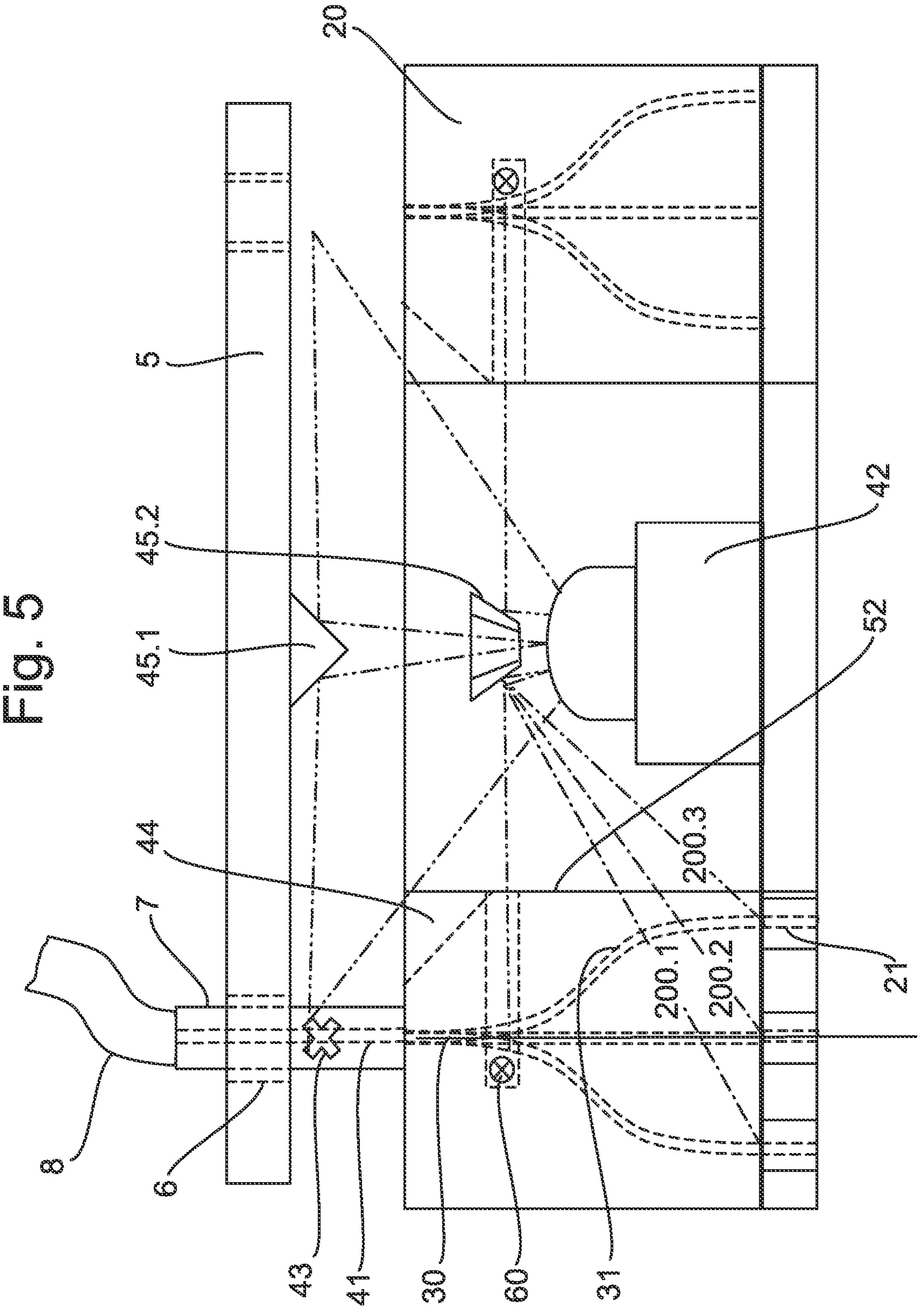
FIG. 5 shows another cross-sectional view of an embodiment of the invention.

In FIG. 5 an embodiment of the invention is shown having the respective connector openings 6 which have received a connector 7 in a correctly mounted recessed position 41, properly aligned and in proximity of the outlet 30. The connectors 7 are marked with one or more markings 43 which become visible to an optical detector 42 when the connectors 7 are in the recessed position 41. These markings 43 may be, geometry circular engravings, patterns, letters or numbers but may also be any other distinguishable marking or coating that could be used to verify the correct (recessed) positioning of a connector or to identify or verify the location of a desired connector 7 and hence a location for treatment. A correct geometry, for instance by means of a chamfer 44, provides a line of sight between the identification marking 43 of the respective connectors 7, when the connectors 7 protrude through the connector plate 5 into the recessed position 41, and an optical detector 42 arranged central to the guiding arrangement 20, so that detector 42 is arranged about central to the guiding arrangement to detect a position of at least one of the selector channels and connector openings, e.g. in a substantial omnidirectional view from a central location, e.g. along a central axis of the selector mechanism 11, so that the number of detectors can be reduced. The purpose of being able to swiftly verify or identify the connectors 7 once they are protruded into the recess is amongst others to verify at which location a connector is inserted, to verify if the connectors are inserted deep enough, and to identify which type of connectors are inserted. This to ensure that the connectors 7 are correctly in place before they are locked, no jamming of the locking occurs, the transport wires 4 are driven out into the planned transport tubes, and the transport tubes are able to receive a driven transport wire 4 without play or deflecting of the wire through a gap resulting from improper seating of the connectors 7. It is optionally possible to shape the guiding arrangement 20 with a chamfer 44 or opening along an inner edge of the guiding arrangement 20 which is closest to the connecting plate 5 such that the line of sight between the optical detector 42 and at least one of the respective connectors 7 and or connector openings 6 is unobstructed by the guiding arrangement 20. It is further possible to use a special optical lens or arrange one or more reflectors 45.1,45.2 along the centre of the guiding arrangement 20 which reflect an image of the content of the at least one guiding channel 31 and/or the respective markings 43 of the connectors 7 to the centre of the guiding arrangement 20. In this way the optical detector can detect the contents of the guiding channels 31 and the markings 43 on the connectors 7 and/or connector openings without the use of multiple detectors as the images of the content and the markings 43 are reflected along the centre of the guiding arrangement 20. It is also possible that the reflectors 45.1,45.2 may be prisms or refractors as well as fibre optical connection or other means known to create a line of sight which changes direction. A slightly different embodiment is to mount the sensor (and also any optical means, if needed) the other way around as depicted in FIGS. 3 to 6 (i.e. looking away from the plate 5/facing more downwards) and to use a wide view angle lens to prevent detection issues due to dust accumulation at the detector or optical elements. It is also possible to optionally provide the selector with at least one light source or to use an optical filter to improve the detectability of the connectors, transport wires or capsules e.g. by means of enhancing the contrast. This can be, for example, a light source that shines towards the areas to be detected (so that the sensor can detect the reflections) or a light source that shines towards the sensor from behind the area to be detected. An embodiment may for example be at least one view port 50 with a light source 60 which radiates both a guiding channel 31, a connector 7, and the optical detector 42. It is also possible that the light source 60 is any other radiator compatible with the optical detector 42 such as an infra red light source. The optical detector 42 may be any other detector or detector assembly which is able to detect the presence, position, identification, movement, or quality of the transport wires 4 and connectors 7 at a distance, such as infra-red sensor, optical sensors, imaging sensors (e.g. CMOS, CCD), photodiodes, photo ICs, PSDs, or camera, whether or not by means of additional software or machine vision algorithms The optical detector 42 also can be used to detect or verify the position of each ring or selector channel with respect to inlet position 21, see lines of sight 200.1, 200.2, 200.3

Figure 6:
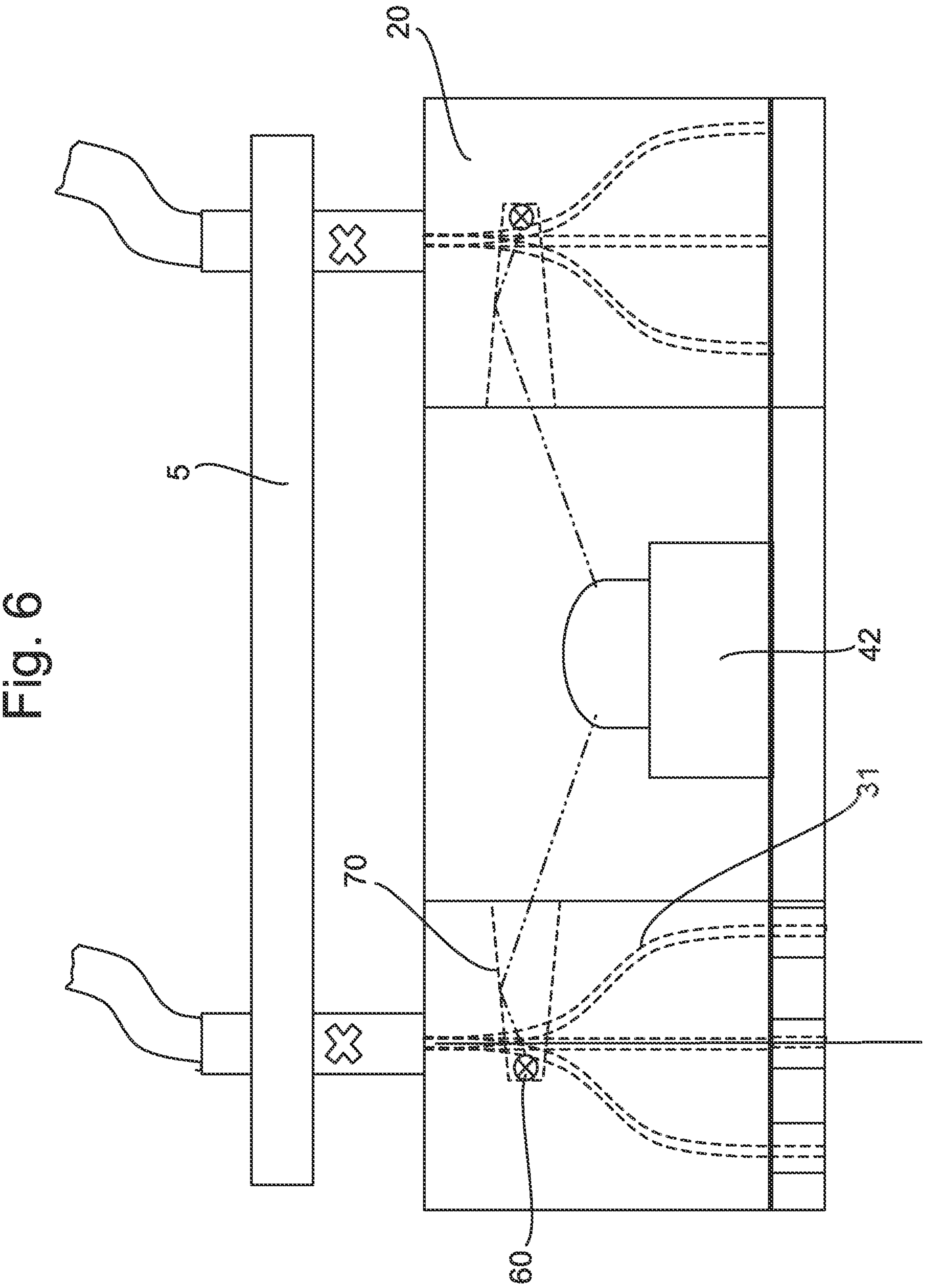
FIG. 6 shows a further cross-sectional view of an embodiment of the invention.

In FIG. 6 another embodiment of the invention is shown in which a view port 70 has a geometry such that at least part of the opening is used to deflect light toward the centre of the guiding arrangement 20 which may contain the optical detector 42. The view port 70 has a reflective surface which reflects an image of the content of the at least one guiding channel 31 to the optical detector 42. E.g. by flaring the view port 70 a wider range of locations for the optical detector 42 is possible as it increases the number of locations from which all the view ports 70 are visible. This may also be useful when the optical detector 42 is additionally used for detecting other criteria such as the markings 43 (shown in FIG. 4) on the connectors 7.

Figure 7:
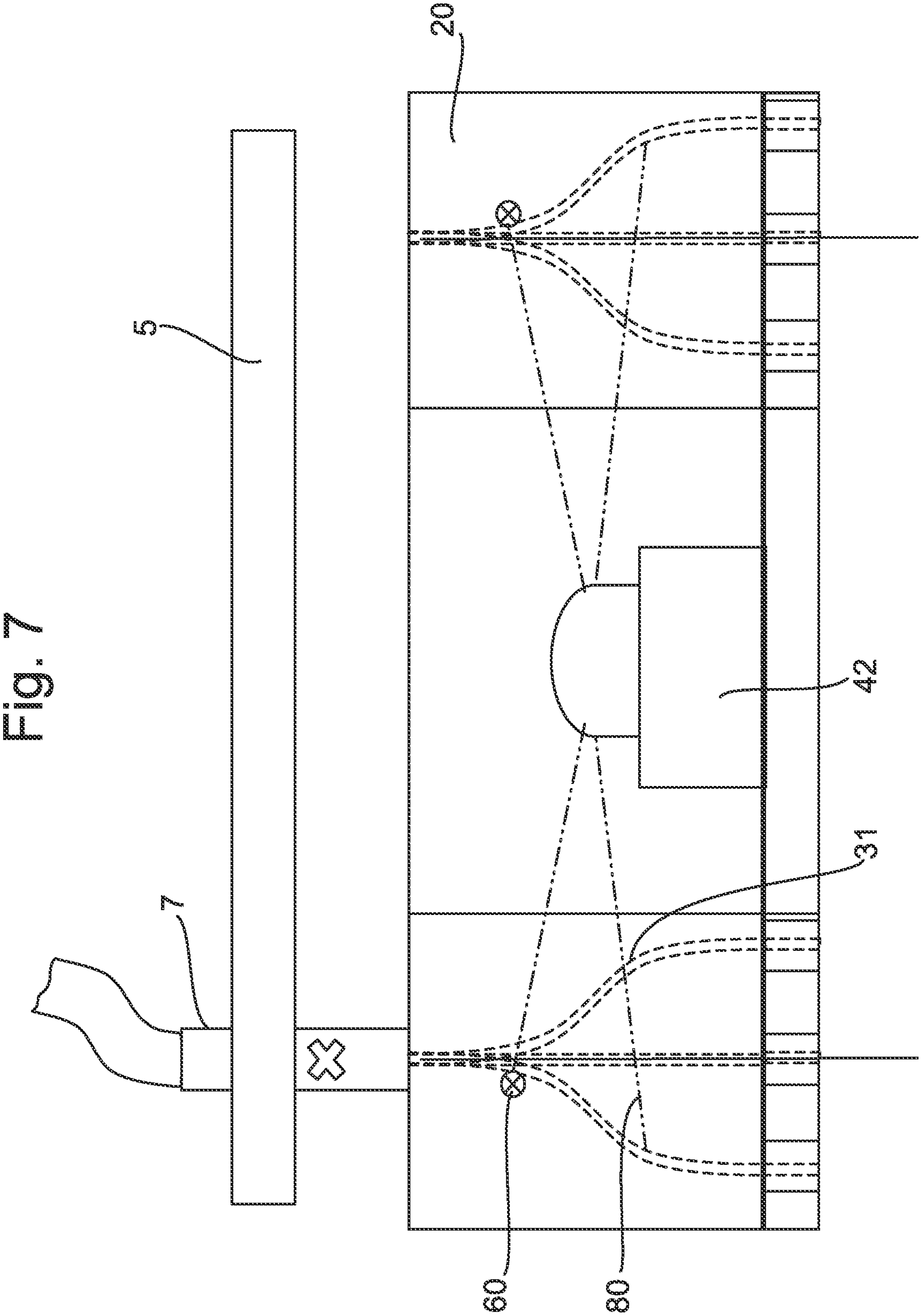
FIG. 7 shows a further cross-sectional view of an embodiment of the invention. with light source.

In FIG. 7 a further embodiment of the invention is shown where the guiding arrangement 20 is transparent (whether or not partially or completely) to allow light 80 to pass through the guiding arrangement 20 and make a content of the respective guiding channels 31 visible to the optical detector 42. By manufacturing (some parts of) the guiding arrangement 20 from transparent materials the entire length of all of the guiding channels 31 may be visible to an optical detector 42.

Figure 8:
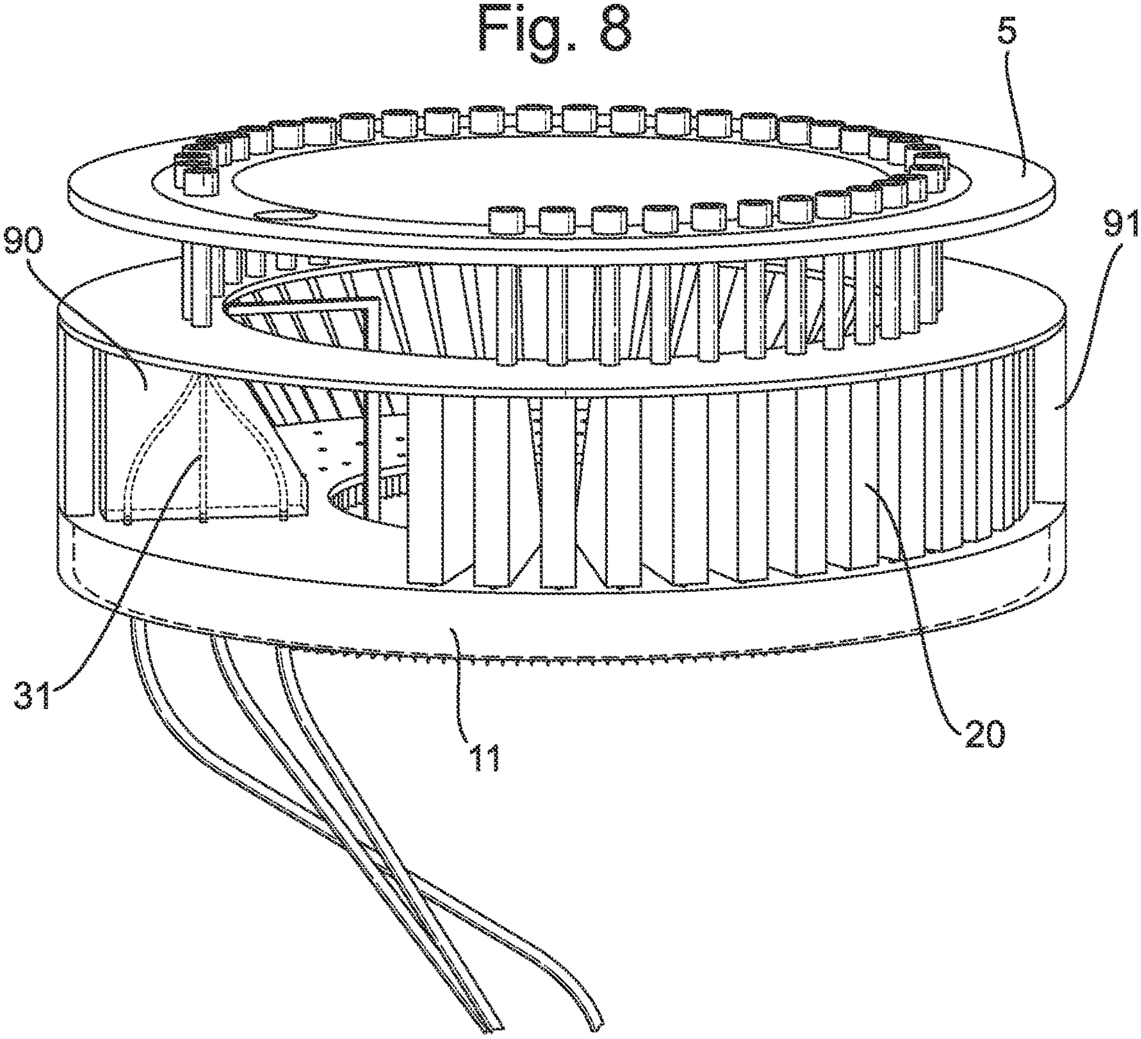
FIG. 8 shows an isometric view of an embodiment of the invention.
Figure 8:
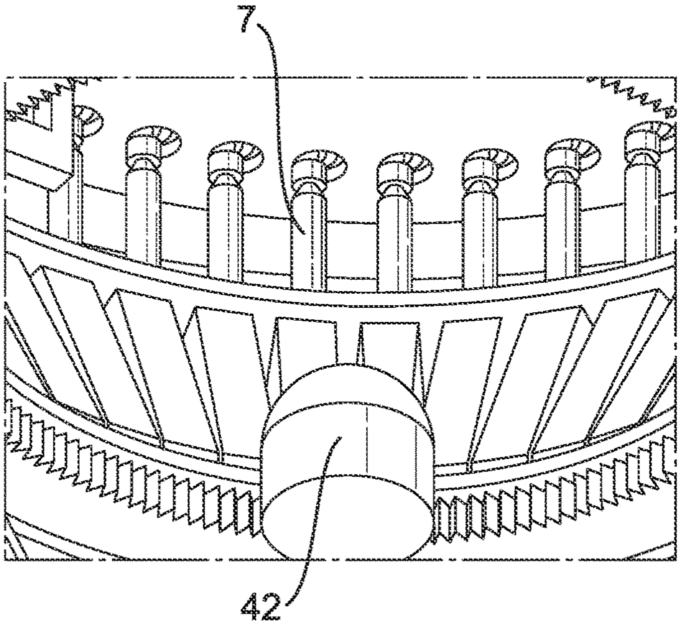

In FIG. 8 an embodiment of the invention is shown in which the guiding arrangement 20 is formed by guiding blocks 90 which are spaced along the circumference. The respective guiding blocks 90 contain the guiding channels 31 which connect at least one of the outlets 30 (FIG. 3) and the respective inlets 21.1,21.2,21.3 (FIG. 2). The guiding blocks 90 are further framed by a guiding block frame 91 which is fixed to the selector frame 11. The guiding blocks 20 may be any shape and are not limited to being cubic or rectangular. A frame is any component able to hold the guiding blocks 20 in place.

An embodiment is to make the guiding blocks 20 from divisible components, so that the required shapes of the guiding channels 31 can be produced better and cheaper.

Figure 9:
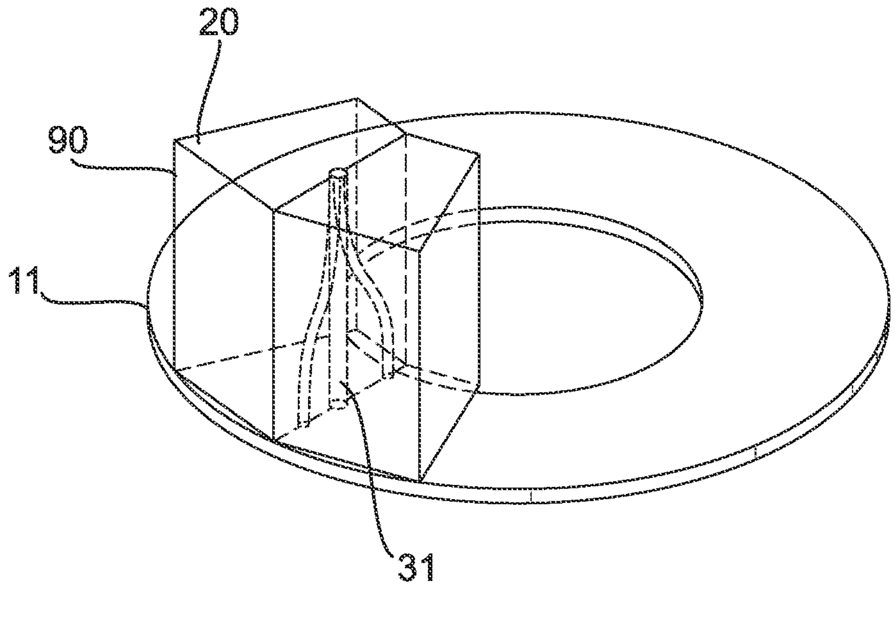
FIG. 9 shows a frame view of an embodiment of the invention.

In FIG. 9 a further embodiment is shown which uses the guiding blocks 90 to establish guiding channels 31 by using the outer surfaces of the guiding blocks 90 as separate parts of the guiding channels 31. So that when guiding blocks are placed against each other or in proximity to each other, the portions of the guiding channels 31 which are contained in the respective guiding blocks 90 work together to form a guiding channel 31. It also facilitates the cleaning of the guiding channels 31 should cleaning be required. Further it may help during maintenance, repairs or upgrades, should a guiding block 20 be damaged or if a guiding block 20 needs replacing due to wear in a guiding channel 31. A guiding channel 31 may also be formed by two or more guiding blocks 20 in series so that the guiding channel 31 in each block 20 aligns with each subsequent guiding block channel 31.

Figure 10:
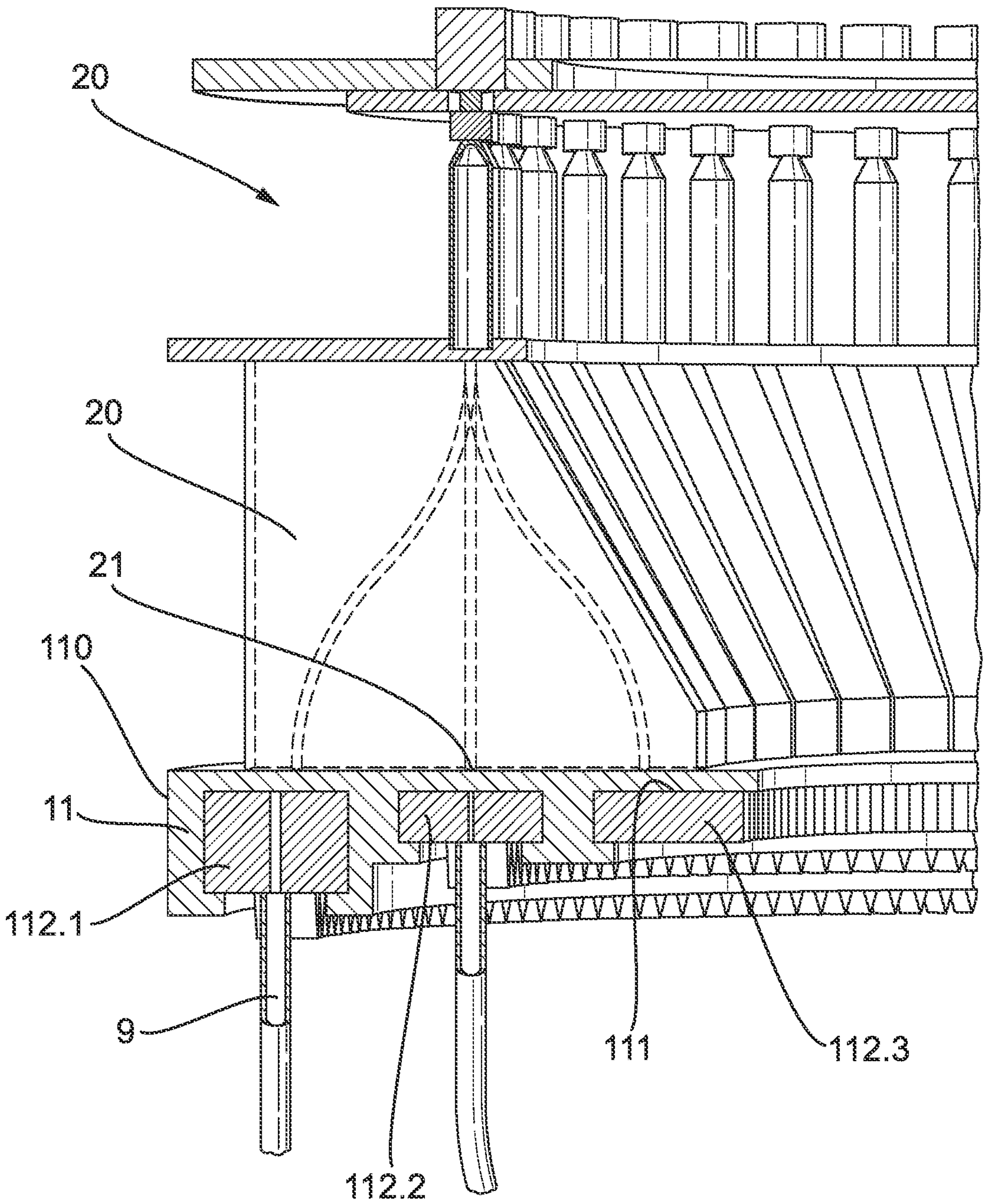
FIG. 10 shows a cross sectional view of an embodiment of the invention.

In FIG. 10 an embodiment of the invention is shown that has the selector mechanism 11 which also has a selector frame 110 with grooves 111. The grooves 111 are used to slidably house a multitude of rotary selector elements, e.g. concentric rings 112. The concentric rings 112 are driven by at least one driving actuator in total (in FIG. 11 one motor per ring is shown as an example) and each selector channel 9 is attached to a respective ring 112. Each of the rings 112 has a radius corresponding to one of the multiple patterns of spaced inlets 21 so that by revolving the rings 112 in the grooves 111, the selector channels 9 can be brought in line with the spaced inlets 21 The alignment of a selector channel 9 with an inlet 21 creates a unique pathway. Along which pathway the transport wire 4 (FIG. 1) can then be driven to a location in the body of a patient via a transport tube 8 (FIG. 1) and applicator 9 (FIG. 1) which corresponds with the chosen inlet 21 in the concentric pattern. The grooves 111 may be other means for constraining the rings 112.1, 112.2, 112.3 to rotate along the desired pattern such as rollers or magnetic tracks or even rails which may or may not be part of the selector frame 11.

Embodiments of one or more rings, or geometries that are not completely closed around are possible, or in which each ring is separately driven, as well as embodiments in which the ring forms part of the drive system.

Figure 11:
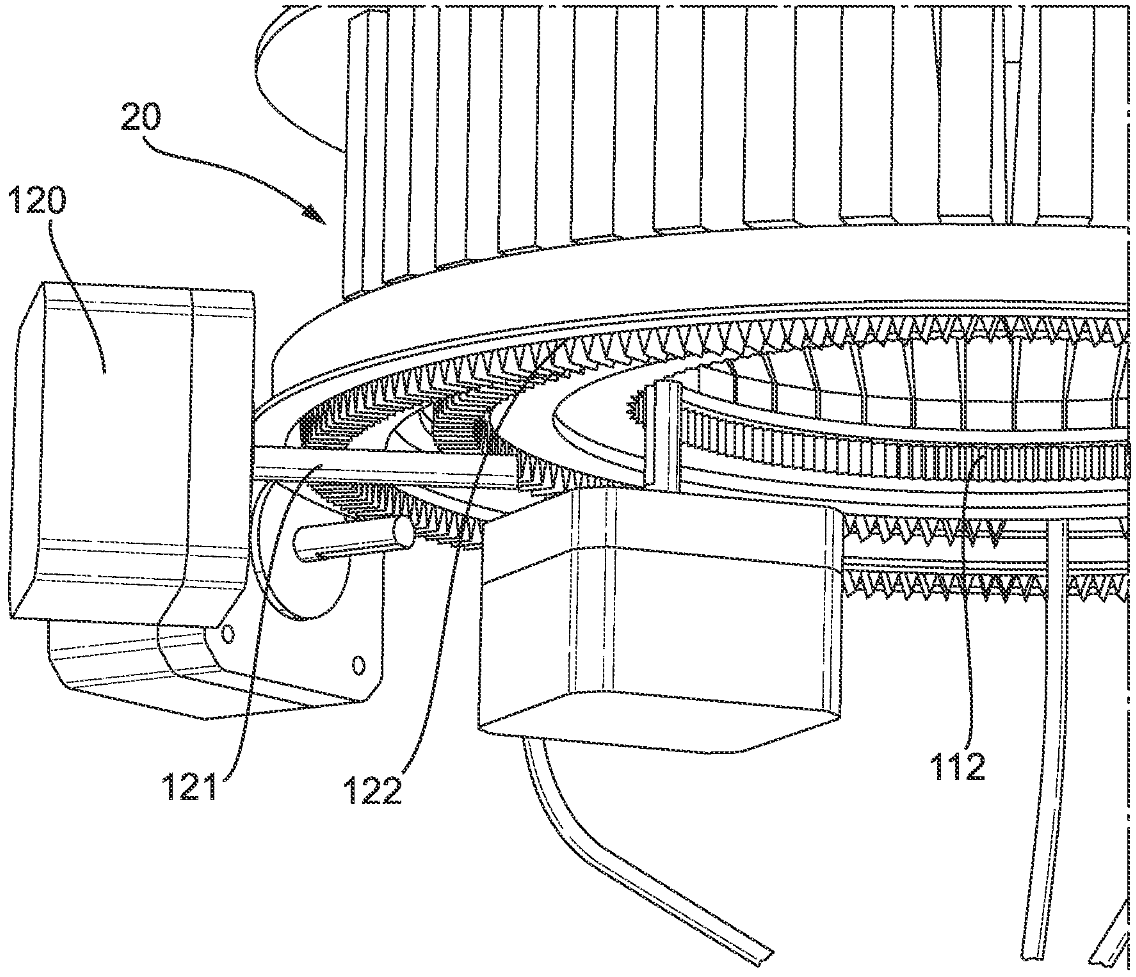
FIG. 11 shows an isometric view of an embodiment of the invention.
Figure 12A:
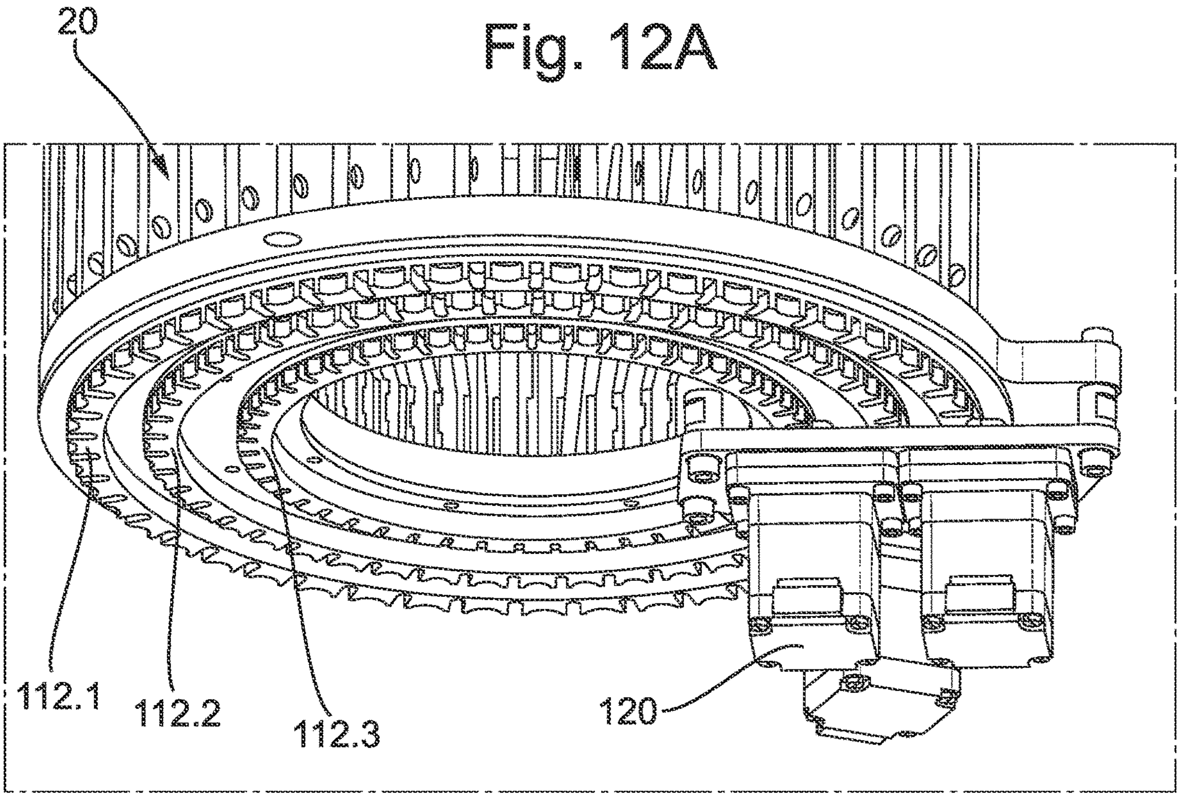
FIG. 12 (A, B) shows an isometric view of an embodiment of the invention.
Figure 12B:
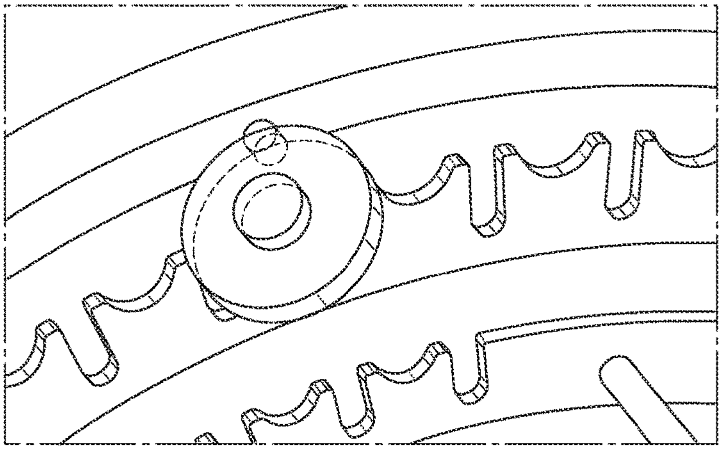

In FIG. 11 a partial view of an embodiment of the invention is shown where the driving actuator 120 may be more than one rotational actuators which have respective rotating shafts 121 with a running surface (not depicted, e.g. a gearwheel) which drives at least one of the rings 112 by rotating the running surface of the actuator or shaft against a driving surface 122 of the rings 112. In FIG. 12 a partial view of an guiding arrangement 20 of the invention is shown where the driven ring 112 has a part of a Geneva wheel integrated and the actuator is a rotating disk with a small pin (FIG. 12B) mounted at the driven shaft of an electromotor 120.

Other means for driving the rings 112 are also possible and may include the concentric rings 112 being driven by magnetic actuators or belt driven arrangements.

Figure 13:
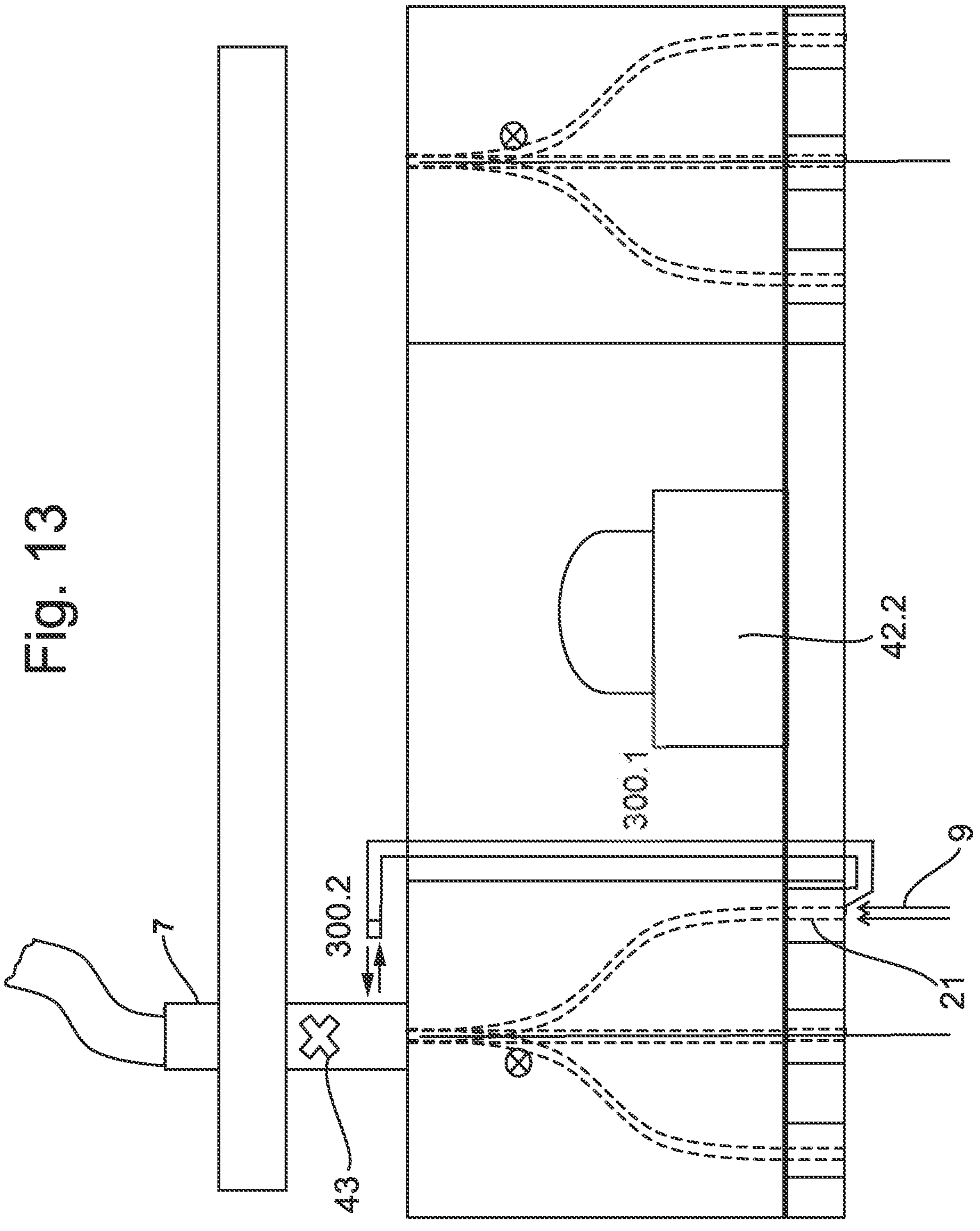
FIG. 13 shows another embodiment of the invention.

FIG. 13 shows an embodiment in which one or more moving optical detectors or optical components are used instead of a stationary central optical detector, this to further improve the detectability of the components, if needed. This can be, for example, a centrally located rotary detector or lens assembly (containing an actuator) 42.2, or a small optical reflectance sensor 300.2 mounted on one of the driven selector rings via a light pad 300.1.

The invention claimed is:

1. A device for transporting and positioning at least one emitting element for therapeutic application into at least one treatment channel to be temporarily placed in or at a body of a patient, the device comprising:

a plurality of transport elements, wherein the at least one emitting element is located in a distal area of at least one transport element of the plurality of transport elements, and wherein the plurality of transport elements are slidable by at least one drive motor, a connecting element comprising multiple connector openings, for connecting a transport tube to a respective connector opening, wherein the transport tube is connectable to the at least one treatment channel for driving the plurality of transport elements through the multiple connector openings and the transport tube to the at least one treatment channel; and a selector mechanism through which the plurality of transport elements are driven, the selector mechanism comprising a plurality of independently displaceable selector channels, wherein each selector channel corresponds to one transport element of the plurality of transport elements, and wherein the plurality of transport elements are driven through the plurality of independently displaceable selector channels for directing the plurality of transport elements into the connecting element, wherein:

the device is provided with a guiding arrangement for guiding the plurality of transport elements into corresponding connector openings in the connecting element;

the guiding arrangement comprises a plurality of spaced outlets in a rear surface thereof facing the connecting element;

each outlet of the plurality of spaced outlets aligns to a respective connector opening of the multiple connector openings in the connecting element to allow the at least one transport element from each outlet to be driven into the respective connector opening;

the guiding arrangement comprises a plurality of inlets in a front surface of the guiding arrangement which faces away from the connecting element said plurality of inlets allowing the at least one transport element from a respective selector channel to be driven into a respective inlet of the plurality of inlets; and each outlet of the plurality of spaced outlets of the guiding arrangement is connected to more than one inlet of the plurality of inlets in the guiding arrangement by one or more guiding channels formed in the guiding arrangement.

2. The device according to claim 1, wherein:

the plurality of inlets in the guiding arrangement are spaced in multiple concentric patterns; and the plurality of independently displaceable selector channels of the selector mechanism are arranged to revolve independently from each other around a central axis to follow the plurality of inlets.

3. The device according to claim 2, wherein;

the selector mechanism comprises a selector frame with multiple grooves which slidably house at least two rotary selector elements to be driven by a driving actuator;

each selector channel is attached to a respective rotary selector element of the at least two rotary selector elements; and each rotary selector element of the at least two rotary selector elements has a radius corresponding to one of the multiple concentric patterns of concentrically spaced inlets.

4. The device according to claim 3, wherein the driving actuator comprises a rotational actuator comprising a rotating element which drives at least one rotary selector element of the at least two rotary selector elements by rotating the rotating element against a driving surface of the at least one rotary selector element.

5. The device according to claim 1, wherein:

the respective connector opening receives a respective connector in a recessed position;

the respective connector comprises a marking;

the recessed position provides a line of sight between the marking of the respective connector, when protruded into the recessed position; and an optical detector is arranged about central to the guiding arrangement.

6. The device according to claim 5, wherein;

the guiding arrangement comprises at least one view port arranged in an inner surface central to the guiding arrangement; and a content of at least one guiding channel of the one or more guiding channels is visible through the at least one view port by the optical detector.

7. The device according to claim 6, wherein a surface of the at least one view port is a reflective surface which reflects an image of at least a part of the content of the at least one guiding channel to the optical detector.

8. The device according to claim 6, wherein at least a part of the guiding arrangement is transparent to allow light to pass through the guiding arrangement and make a content of the at least one guiding channel of the one or more guiding channels visible to the optical detector.

9. The device according to claim 5, further comprising:

at least one of: i) at least one light source or ii) at least one filter to enhance detectability of the respective connector, the at least one transport element, the at least one emitting element, one or more capsules, one or more rotary selector elements, one or more selector channels, or one or more components attached to one of the one or more rotary selector elements or selector channels.

10. The device according to claim 5, wherein the optical detector is arranged to detect a position of at least one of: at least one selector channel of the plurality of independently displaceable selector channels, ji) one or more rotary selector elements, or iii) one or more components attached to the at least one selector channel of the plurality of independently displaceable selector channels or the one or more rotary selector elements.

11. The device according to claim 1, wherein:

the guiding arrangement comprises several guiding blocks placed in a circular shape;

one or more respective guiding blocks of the several guiding blocks comprise the one or more guiding channels and at least one outlet of the plurality of spaced outlets and the respective inlet which are connected thereby; and the several guiding blocks are framed by a guiding block frame which is fixed to a selector frame.

12. The device according to claim 11, wherein the one or more guiding channels are formed by making the one or more respective guiding blocks of the several guiding blocks from more than one component.

* * * * *